United States Patent [19]

Bergersen

[11] Patent Number: 4,784,605
[45] Date of Patent: Nov. 15, 1988

[54] ORTHODONTIC APPLIANCE TO CORRECT OPEN-BITE TENDENCIES IN CHILDREN AND ADULTS AND TONGUE-THRUST IN YOUNG CHILDREN

[76] Inventor: Earl O. Bergersen, 950 Green Bay Rd., Winnetka, Ill. 60093

[21] Appl. No.: 108,086
[22] Filed: Oct. 13, 1987
[51] Int. Cl.$^4$ .............................................. A61C 7/00
[52] U.S. Cl. ....................................................... 433/6
[58] Field of Search ......................................... 433/6, 7

[56] References Cited
FOREIGN PATENT DOCUMENTS 2461180 7/1945 Fed. Rep. of Germany .......... 433/6
1085421 7/1954 France ................................... 433/6

Primary Examiner—Robert Peshock

[57] ABSTRACT

An orthodontic tooth positioning appliance is provided for correcting open-bite which includes a web region engageable by the posterior teeth to prevent further eruption of those teeth and a vertical gap between the occlusal surfaces of the anterior teeth to permit further eruption of those teeth. The appliance may also include a tongue guide profile including at least one pointed protrusion on the lingual side of the lower midline portion of the appliance and a recessed area above the protrusion for receiving a tip of the tongue.

21 Claims, 1 Drawing Sheet

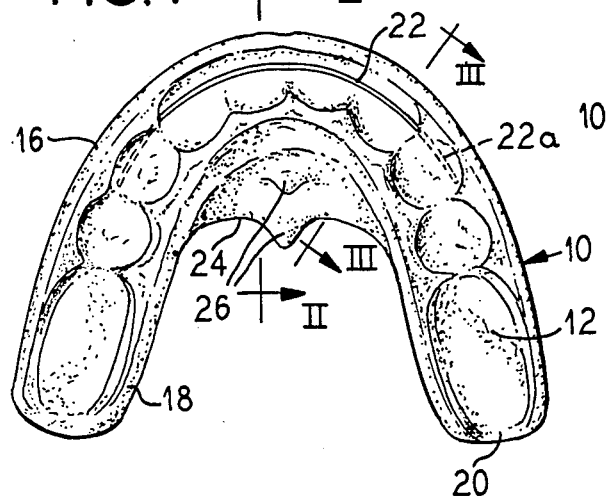
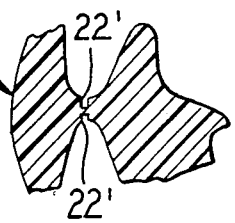
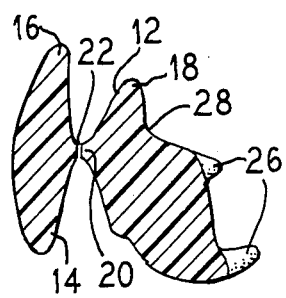
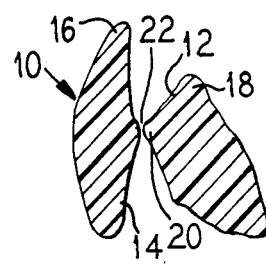
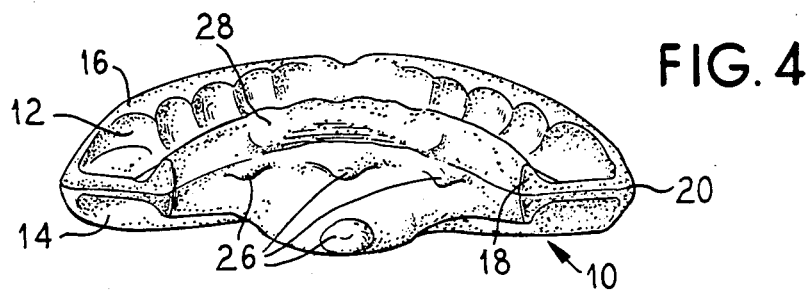
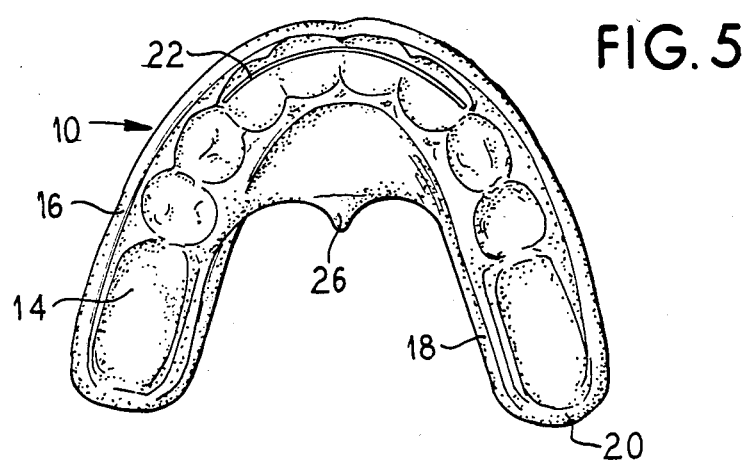

ORTHODONTIC APPLIANCE TO CORRECT OPEN-BITE TENDENCIES IN CHILDREN AND ADULTS AND TONGUE-THRUST IN YOUNG CHILDREN

BACKGROUND OF THE INVENTION

1. Field of the Invention

The present invention relates to appliances for correcting human dentition and more particularly to an appliance for correcting open-bite and tongue-thrust.

2. Description of the Prior Art

Open bites are quite prevalent in young children, open bite being the condition where the posterior teeth erupt to a greater degree than the anterior teeth so that when occlusion occurs, only the posterior teeth are in contact, the anterior teeth being open. Tongue thrusting, that is the pressing of the tongue against the anterior teeth, frequently accompanies the problem of open bite.

It would be beneficial to have a preformed appliance to correct the problem of open bite and to correct the anterior tongue thrust problem.

SUMMARY OF THE INVENTION

The present invention provides a device which is a preformed appliance, removable and insertable by the user which can be used to correct the problem of open bite in children and adults and can also be used to correct anterior tongue thrust.

The appliance is a generally U-shaped device with an isthmus portion forming the U-shape and the sides of the isthmus being vertical flanges, the outer flange being a labial-buccal flange and the interior flange being a lingual flange. Such an appliance is described in my prior U.S. Pat. No. 3,939,598. Individual sockets are provided to receive each of the teeth.

A structural difference between the appliance embodying the principles of the present invention over my prior device is that in the new appliance there is a narrow slit or recess provided vertically between the upper and lower incisors so that no pressure is applied on these teeth vertically when the user bites vertically. In a child, there is only pressure on the deciduous canines and molars when the child bites the appliance with pressure. This depresses the posterior teeth and reduces the vertical dimension between the jaws and helps to deepen the anterior open bite. The appliance is made of a resilient moldable material which may be of selected durometer to depress the posterior teeth most effectively.

Such an appliance can also be utilized by adults where all permanent teeth are present. The posterior teeth (second and first permanent molars and permanent bicuspids) have a soft resilient material between them occlusally, while the permanent anterior teeth (canine, lateral and central incisors) have a slit vertically so that no depression is placed on them during biting forces and will therefore encourage their eruption and correction of an open-bite. This appliance can also aid in the maintenance of a stable vertical face and mandibular plane angle during standard fixed-appliance treatment involving long-faced individuals with steep mandibular plane angles. In these appliances, the material can be cleared out or removed horizontally on the interior or reduced vertically to allow the fixed-appliance brackets to be accomodated within the sockets of the appliance.

To aid in the correction of the anterior tongue-thrust problem a small inset circle is molded into the anterior region of the appliance as a reminder guide for the tip of the tongue as well as a curved area to encourage the tongue to assume a more vertical position together with a pointed protrusion from the lingual side of the lower midline portion of the appliance to discourage the tongue from assuming an anterior and depressed position while sleeping.

BRIEF DESCRIPTION OF THE DRAWINGS

FIG. 1 is a plan view of an appliance embodying the principles of the present invention.

FIG. 2 is a sectional view taken generally along the lines II—II of FIG. 1.

FIG. 3 is a sectional view taken generally along the lines III—III of FIG. 1.

FIG. 4 is a rear view of the appliance of FIG. 1.

FIG. 5 is a bottom view of the appliance of FIG. 1.

DESCRIPTION OF THE PREFERRED EMBODIMENTS

An orthodontic appliance embodying the principles of the present invention is shown generally at 10 in FIGS. 1-5. The appliance is in the form of an orthodontic positioner somewhat similar to the positioner I describe in my U.S. Pat. No. 3,939,598 in that the positioner is U-shaped in plan view with a bight at an anterior portion and free ends at two posterior portions and includes an upper trough 12 for receiving the maxillary teeth and a lower trough 14 for receiving the mandibular teeth. The troughs are formed generally by a labial-buccal flange 16 and a lingual flange 18, these flanges being connected by an isthmus or web portion 20 which interconnects the two flanges. Both the upper and lower troughs are provided with tooth receiving depressions or sockets, which sockets may receive one or more teeth. The appliance preferably is preformed for fitting a plurality of different patients within a given size range.

A vertical slit 22 is provided in the isthmus 20 in the region of the sockets for at least the incisors as shown in solid lines in FIG. 1 and, in some cases to include the socket region for the canines (usually for adult usage) as illustrated at 22a by dashed lines in FIG. 1.

It should be understood that the slit may be a through-slit 22 (as shown in FIGS. 2 and 3) which extends completely through the appliance, or it may be an opposed pair of channels or a recesses or a partial slit 22' (as shown in FIG. 2A) so long as it is sized and shaped to allow the teeth to erupt vertically without resistance. In this manner the isthmus interconnects the flanges only in the posterior portion of the appliance and does not interconnect the flanges in the anterior portion. The vertical slit 22 ensures that no pressure will be applied to the incisors (and possibly canines) in a vertical direction when the user of the appliance bites thereon. The isthmus 20 which is solid in the region of the posterior teeth will prevent further eruption of those teeth while the slit will encourage further eruption of the anterior teeth to assist in the correction of the open bite condition.

The appliance also includes a molded inset 24 which preferably is molded integrally with the appliance, the inset being molded into the anterior region of the appliance on the lingual side as a reminder guide for the tip of the tongue. The inset 24 includes one or more pointed protrusions 26 which may be positioned along the lower midline portion of the appliance or laterally spaced from the midline, on the lingual side, to discourage the tongue from assuming an anterior and depressed position. The contour of the appliance along the midline, as best seen in FIG. 2, also includes a recessed area 28 superior to the protrusions 26 which encourages the tongue to assume a higher vertical position especially when used in combination with the pointed protrusions 26. The addition of this molded insert serves to encourage proper tongue positioning, thereby overcoming the anterior tongue-thrust problem which tends to worsen the open bite condition.

The appliance is made of a resilient moldable material to provide a soft cushioning engagement with the posterior teeth as they contact the isthmus in the posterior region of the appliance to depress the posterior teeth.

The sockets in the troughs can be enlarged by clearing out the material horizontally on the interior or reducing the vertical height of the appliance to permit the appliance to be used by persons having fixed-appliances on their teeth, the enlarged socket areas allowing the fixed appliance brackets to be accomodated therein.

The present invention is also applicable to a positioner having only an upper trough or only a lower trough, in either event the vertical slit will be provided at the anterior region of the positioner to avoid vertical pressure on the anterior teeth.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An orthodontic tooth positioning appliance which is generally U-shaped in plan view and which includes at least one tooth receiving trough of a size and shape for positioning at least one row of a patient's upper and lower row of teeth of sufficient length to include incisors and canines, said trough being defined by lingual and labial-buccal flanges and including an isthmus interconnecting said flanges;

said isthmus having a vertical slit along less than an entirety of the length of said appliance in an anterior portion of said appliance which is engaged by at least some of the central incisor, lateral incisor and canine anterior teeth.

2. An orthodontic tooth positioning appliance according to claim 1, wherein said vertical slit is limited to the region of the incisors.

3. An orthodontic tooth positioning appliance according to claim 1, wherein said vertical slit extends laterally to include the canines.

4. An orthodontic tooth positioning appliance which is generally U-shaped in plan view and which includes at least one tooth receiving trough of a size and shape for positioning at least one row of a patient's upper and lower row of teeth of sufficient length to include incisors and canines, said trough being defined by lingual and labial-buccal flanges and including an isthmus interconnecting said flanges;

said isthmus having a vertical slit in an anterior portion of said appliance which is engaged by at least some of the central incisor, lateral incisor and canine anterior teeth; and means for guiding the tongue including at least one pointed protrusion formed on the lingual side of the lower midline portion of the appliance and a recessed area superior to the protrusion for receiving a tip of the tongue.

5. An orthodontic tooth positioning appliance according to claim 4, wherein two pointed protrusions are formed on said appliance in vertical alignment.

6. An orthodontic tooth positioning appliance according to claim 4, wherein two pointed protrusions are formed on said appliance in horizontal alignment.

7. An orthodontic tooth positioning appliance according to claim 4, wherein said vertical slit extends vertically through said isthmus.

8. An orthodontic tooth positioning appliance according to claim 1, wherein said vertical slit is sized and shaped in such a manner that the teeth in register therewith may erupt vertically without resistance.

9. An orthodontic tooth positioning appliance according to claim 1, wherein the appliance includes a trough for treating the mandibular teeth and a trough for treating the maxillary teeth.

10. An orthodontic tooth positioning appliance according to claim 1, wherein the appliance is a preformed appliance constructed for fitting a plurality of different patients within a given size range.

11. An orthodontic tooth positioning appliance which is generally U-shaped in plan view with a bight at an anterior portion and free ends at two posterior portions and which includes at least one tooth receiving trough of a size and shape for positioning at least one row of a patient's upper and lower row of teeth, said trough being defined by lingual and labial-buccal flanges and having a web interconnecting said flanges, said web interconnecting said flanges only in the posterior portions of said appliance to engage posterior teeth so as to prevent further eruption of those teeth.

12. An orthodontic tooth positioning appliance according to claim 11, wherein the interconnection of said flanges by said web ends posterior to a region engaged by the canines.

13. An orthodontic tooth positioning appliance according to claim 11, wherein the interconnection of said flanges by said web ends anterior to a region engaged by the canines.

14. An orthodontic tooth positioning appliance which is generally U-shaped in plan view with a bight at an anterior portion and free ends at two posterior portions and which includes at least one tooth receiving trough of a size and shape for positioning at least one row of a patient's upper and lower row of teeth, said trough being defined by lingual and labial-buccal flanges and having a web interconnecting said flanges, said web interconnecting said flanges only in the posterior portions of said appliance; and means for guiding the tongue including at least one pointed protrusion formed on the lingual side of the lower midline portion of the appliance and a recessed area superior to the protrusion for receiving a tip of the tongue.

15. An orthodontic tooth positioning appliance according to claim 14, wherein two pointed protrusions are formed on said appliance in vertical alignment.

16. An orthodontic tooth positioning appliance according to claim 14, wherein two pointed protrusions are formed on said appliance in horizontal alignment.

17. An orthodontic tooth positioning appliance according to claim 11, wherein the appliance includes a trough for treating the mandibular teeth and a trough for treating the maxillary teeth.

18. An orthodontic tooth positioning appliance according to claim 11, wherein the appliance is a preformed appliance constructed for fitting a plurality of different patients within a given size range.

19. An orthodontic tooth positioning appliance which is generally U-shaped in plan view with a bight at an anterior portion and free ends at two posterior portions and which includes at least one tooth receiving trough of a size and shape for positioning at least one row of a patient's upper and lower row of teeth, said trough being defined by lingual and labial-buccal flanges and having a web interconnecting said flanges, said web including a pair of vertically opposed channels in an anterior portion of said appliance.

20. An orthodontic tooth positioning appliance according to claim 19, wherein said channels end anterior to a region engaged by the canines.

21. An orthodontic tooth positioning appliance according to claim 19, wherein said channels end posterior to a region engaged by the canines.

* * * * *